_US005070064A_

United States Patent [19]

Hsu et al.

[11] Patent Number: 5,070,064

[45] Date of Patent: Dec. 3, 1991

[54] CATALYST PRETREATMENT METHOD

[75] Inventors: Edward C. Hsu, Bridgewater; John L. Robbins, Stockton, both of N.J.

[73] Assignee: Exxon Research and Engineering Company, Florham Park, N.J.

[21] Appl. No.: 389,916

[22] Filed: Aug. 7, 1989

[51] Int. Cl.$^5$ .................. B01J 21/06; B01J 23/70; C07C 1/04; B03B 5/30

[52] U.S. Cl. ............................ 502/325; 209/171; 209/172.5; 502/21; 502/31; 502/33; 502/258; 502/260; 502/332; 518/715

[58] Field of Search ................... 502/21, 31, 33, 325; 209/171, 172, 172.5; 210/806, 807

[56] References Cited

U.S. PATENT DOCUMENTS

| | | | |
|---|---|---|---|
| 2,601,121 | 6/1952 | Mattox | 518/720 |
| 2,991,878 | 7/1965 | Gary | 209/172.5 |
| 3,213,033 | 10/1965 | Hindin et al. | 502/30 |
| 4,568,663 | 2/1986 | Mauldin | 502/325 |
| 4,605,678 | 8/1986 | Brenman et al. | 518/700 |
| 4,714,553 | 12/1987 | Crovzet | 209/172 |
| 4,714,693 | 12/1987 | Targos | 502/325 |
| 4,818,417 | 4/1989 | Crouzet | 210/806 |
| 4,857,559 | 8/1989 | Eri et al. | 518/700 |
| 4,931,193 | 6/1990 | Crouzet | 210/806 |

*Primary Examiner*—Paul E. Konopka
*Attorney, Agent, or Firm*—Jay Simon

[57] ABSTRACT

An improved pretreatment method for preparing powdered catalysts with well controlled particle size distributions that are free of sub 1 micron particles comprising dispersion of the powdered catalyst in liquid comprised of either a) a hydrocarbon containing low levels of a surfactant or, b) a surfactant containing polar protic solvent, followed by decantation of the suspended finely divided sub 1 micron particles and repeating said sequence until essentially 90% of the sub 1 micron particles have been removed.

10 Claims, No Drawings

CATALYST PRETREATMENT METHOD

FIELD OF INVENTION

This invention relates to an improved procedure for preparing powdered catalysts and to process improvements obtained therewith. More particularly, this invention relates to a method for removing finely divided particles from catalyst or catalyst carrier particles of greater than 1 micron. Still more particularly, this invention relates to a method in which catalyst particles are dispersed in a suitable liquid and finely divided, sub-micron particles are separated from the catalyst particles.

BACKGROUND OF THE INVENTION

The Fischer-Tropsch reaction involves the catalytic hydrogenation of carbon monoxide to produce a variety of products ranging from methane to higher aliphatic alcohols. The methanation reaction was first described by Sabatier and Senderens in 1902. The later work of Fischer and Tropsch dealing with higher hydrocarbon synthesis was described in Brennstoff-Chem, 7, 97 (1926).

The reaction is highly exothermic and care must be taken to design reactors for adequate heat exchange capacity as well as the ability to continuously produce and remove the desired range of hydrocarbon products. The process has been considered for the conversion of carbonaceous feedstocks, e.g., coal or natural gas, to higher value liquid fuel or petrochemicals. The first major commercial use of the Fischer-Tropsch process was in Germany during the 1930's. More than 10,000 B/D of products were manufactured with a cobalt based catalyst in a fixed-bed reactor. This work has been described by Fischer and Pichler in German Patent No. 731,295 issued Aug. 2, 1936.

Commercial practice of the Fischer-Tropsch process has continued in South Africa in the SASOL plants. These plants use iron based catalysts and produce gasoline in fluid-bed reactors and wax in fixed-bed reactors.

Research aimed at the development of more efficient CO hydrogenation catalysts and reactor systems is continuing. In particular, a number of studies describe the behavior of iron, cobalt or ruthenium based catalysts in slurry reactors together with the development of catalyst compositions and improved pretreatment methods specifically tailored for that mode of operation.

Farley et al in The Institute of Petroleum, vol. 50, No. 482, pp. 27-46, February (1984) describe the design and operation of a pilot-scale slurry reactor for hydrocarbon synthesis. Their catalysts consisted of precipitated iron oxide incorporating small amounts of potassium and copper oxides as promoters. These catalysts underwent both chemical and physical changes during activation with synthesis gas in the slurry reactor.

Slegeir et al in Prepr. ACS Div. Fuel Chem, vol. 27, p. 157-163 (1982) describe the use of supported cobalt catalysts for the production of hydrocarbons from synthesis gas at pressures above 500 psi in a continuous stirred tank (CSTR) slurry reactor.

Brennan et al in U.S. Pat. No. 4,605,678 issued on Aug. 12, 1986 describe a process for removing catalyst fines from the wax product produced in a slurry Fischer-Tropsch reactor. Their process comprises removing the wax product from the reactor and separating the catalyst fines by passing the wax through a high gradient magnetic field, whereby the catalyst fines are held by a magnetized filter element and the wax product passes through unhindered to form a purified wax product. The separated catalyst fines are returned to the reactor by backwashing the filter element.

Rice et al in U.S. Pat. No. 4,659,681 issued on Apr. 21, 1987 describe the laser synthesis of iron based catalyst particles in the 1-100 micron particle size range for use in a slurry Fischer-Tropsch reactor.

Dyer et al in U.S. Pat. No. 4,619,910 issued on Oct. 28, 1986 and U.S. Pat. No. 4,670,472 issued on June 2, 1987 and U.S. Pat. No. 4,681,867 issued on July 21, 1987 describe a series of catalysts for use in a slurry Fischer-Tropsch process in which synthesis gas is selectively converted to higher hydrocarbons of relatively narrow carbon number range. Reactions of the catalyst with air and water and calcination are specifically avoided in the catalyst preparation procedure. Their catalysts are activated in a fixed-bed reactor by reaction with $CO+H_2$ prior to slurrying in the oil phase in the absence of air.

Fujimoto et al in Bull. Chem. Soc. Japan, vol. 60, pp. 2237-2243 (1987) discuss the behavior of supported ruthenium catalysts in slurry Fischer-Tropsch synthesis. They indicate that the catalyst precursors were ground to fine powders (<150 mesh), calcined if needed, and then activated in flowing hydrogen before addition to a degassed solvent and subsequent introduction to the slurry reactor.

The organic product for the slurry Fischer-Tropsch process contains olefins; paraffins and oxygenated hydrocarbons with carbon numbers from 1 to well over 100. Only those compounds with high vapor pressure at reaction conditions will readily be removed with the effluent gas stream. The relatively non-volatile molecules such as C20+ paraffin wax will remain in the slurry oil phase. During continuous operation it is necessary to remove these non-volatile products in a continuous manner in order to prevent excessive build-up in the reaction zone. This is especially important if the process is being conducted for the selective production of these high molecular weight (non-volatile) hydrocarbons.

Farley et al (vida supra) conducted numerous laboratory tests to determine the best method by which to withdraw Fischer-Tropsch wax from a slurry reactor, which was both capable of high withdrawal rates and yet would efficiently retain the catalyst within the reaction system for subsequent use. Magnetic separation techniques, sintered metal and woven metal filters were shown to be unacceptable for use at the severe temperatures and pressures used. These systems gave limited filter flux rates (quantity of wax filtered per unit of filter surface area per unit of time) that was probably due to partial plugging of the filter by the powdered iron based catalysts that were being used.

An object of this invention is the preparation of a powdered catalyst which is free of sub 1 micron particles, for use in a continuous Fischer-Tropsch process for the production and continuous withdrawal of hydrocarbon wax. The use of the pretreatment procedure of the instant invention precludes the need for the complex and costly magnetic separation schemes that have been disclosed and allows the use of relatively inexpensive filtration techniques that have heretofore been shown to be of difficult and therefore of marginal utility.

This invention is applicable to catalyst or carrier wherein sub micron particles adhere to the catalyst or carrier particles as a result of the carrier or catalyst preparation. Thus, inorganic oxide carriers of appropriate size may be prepared by crushing or grinding techniques well known to the art. Catalytic metals are then incorporated onto the particles. Alternatively, catalysts may be prepared by incorporating catalytic metals onto particulate carriers of a relatively larger size and then the catalyst is crushed or ground to form the powdered catalyst of appropriate size. During the crushing or grinding steps the mechanical sizing step, very fine submicron particles are formed that tend to adhere to the catalyst and carrier particles.

SUMMARY OF THE INVENTION

Powdered catalysts useful in a wide variety of liquid phase processes, particularly liquid phase Fischer-Tropsch processes, can be prepared free of sub micron particles formed during catalyst or carrier preparation procedures by a method comprising dispersing the catalyst particles in a liquid medium that may be either (a) a $C_5+$ hydrocarbon or mixtures thereof with a surfactant like material, e.g., $H_2O$, or (b) a mixture of a surfactant and protic solvent, agitating the mixture and causing the sub micron particles to separate from the catalyst or carrier particles and concentrate in the liquid phase, and separating the liquid phase containing the sub micron particles from the solid (catalyst or carrier) phase. The method may be carried out in one or more cycles wherein the first cycle comprises dispersing, agitating, concentrating and separating and successive cycles wherein the dispersing step may or may not be included because not all of the liquid phase has been removed.

The dispersing step requires that a liquid phase is present, even though some hydrocarbons are solid rather than liquid at room temperature. Regardless of the phase of the diluent, the method is effected in the liquid phase which is most easily accomplished by raising the temperature of the particles and diluent such that a liquid phase forms and the particles are dispersed therein.

In a preferred embodiment of this invention, Fischer-Tropsch catalysts are prepared which are substantially free of sub micron particles. These catalysts contain a Group VIII catalytic metal, such as cobalt, ruthenium, iron, or nickel in concentrations of about 1-50% by weight supported on an inorganic, refractory oxide support, such as titania, silica, alumina, silica-alumina, titania-alumina or other Group VA or Group VI metal oxides. The catalyst may also contain one or more promoters or additional metals or metal oxides from Group I, Group II, Group V, Group VII or Group VIII in concentrations of 1 to 100% by weight of the catalytic metal. Preferred catalysts include cobalt, cobalt and thoria, cobalt and rhenium; while preferred supports include titania, titania-alumina, silica, or alumina, but most preferably predominantly titania. When a cobalt-rhenium catalyst is employed, the cobalt is present in amounts ranging from about 2-50% by weight, preferably 2-20 wt %, and the rhenium:cobalt weight ratio is greater than 0.01, preferably 0.01 to 1.0, more preferably 0.025:1 to 0.1 to 1.0.

When the support material is comprised of major amounts of titania, the titania preferably has a rutile:anatase ratio of at least about 2:3 as determined by x-ray diffraction (ASTM D2730-78), preferably about 2:3 to about 100:1 or higher, more preferably about 4:1 to 100:1 or higher, e.g., 100% rutile. The surface area of the preferred support is, generally, less than about 50 $m^2/gm$ (BET).

While the invention described herein refers to finished catalyst particles, that is, particles comprising the catalytic metals and the carrier, this invention is also applicable to removing sub micron particles from carrier particles prior to incorporating the catalytic metals. All of the procedures described herein are identical, regardless of whether or not the metals have been incorporated onto the carrier.

DETAILED DESCRIPTION

The instant invention involves a pretreatment method for powdered 1-200 micron diameter catalyst particles with a hydrocarbon containing low levels of oxygenated molecules, or polar protic liquids containing surfactants, followed by removal of the finely divided sub 1 micron containing phase via decantation, siphoning or other physical separation procedures. Use of this pretreatment method leads to an improved catalyst for slurry Fischer-Tropsch synthesis of paraffin wax. This procedure effectively serves to remove the sub 1 micron particles that would otherwise interfere with relatively economic catalyst-product separation procedures such as filtration through sintered metal mesh, woven metal fibers, or other filtration materials such as glass fibers, cloth, fibrous carbon, microporous teflon membranes, or other commercially available filtration materials.

Cobalt-rhenium/titania catalysts exhibit high selectivity in the synthesis of hydrocarbon liquids from carbon monoxide and hydrogen. The catalysts employed in the practice of this invention may be prepared by techniques known in the art for the preparation of other catalysts. The catalyst powder can, e.g., be prepared by gellation, or cogellation techniques. Suitably, however, the metals can be deposited on a previously pilled, pelleted, beaded, extruded, or sieved support material by the impregnation method. In preparing catalysts, the metals are deposited from solution on the support in preselected amounts to provide the desired absolute amounts, and weight ratio of the respective metals, cobalt and rhenium. Suitably, the cobalt and rhenium are composited with the support by contacting the support with a solution of a cobalt containing compound, or salt, or a rhenium-containing compound, or salt, e.g., a nitrate, carbonate or the like. Optionally, the cobalt and rhenium can be coimpregnated on the support. The cobalt and rhenium compounds used in the impregnation can be any organometallic or inorganic compounds which decompose upon heating in nitrogen, argon, helium or other inert gas, calcination in an oxygen containing gas, or treatment with hydrogen at elevated temperatures to give the corresponding metal, metal oxide, or mixtures of the metal and metal oxide phases, of cobalt and rhenium. Cobalt and rhenium compounds such at the nitrate, acetate, acetylacetonate, naphthenate, carbonyl, or the like can be used. The amount of impregnation solution should be sufficient to completely wet the carrier, usually within the range from about 1 to 20 times of the carrier by volume, depending on the metal, or metals, concentration in the impregnation solution. The impregnation treatment can be carried out under a wide range of conditions including ambient or elevated temperatures.

The catalyst, after impregnation, is dried by heating at a temperature above 30° C., preferably between 30°

C. and 125° C., in the presence of nitrogen, or oxygen, or both, or air, in a gas stream or under partial vacuum.

The catalyst particles, if necessary, are converted to the desired particle size range of nominally 1-200 microns average diameter by mechanical methods, e.g., crushing, grinding, ultrasonic treatment, or other methods known to those skilled in the art. The material can then be sieved, if necessary, to produce a powder that is predominantly within the desired particle size range. The presence of finely divided sub 1 micron particles in this sieved fraction poses a major problem in producing the desired 1-200 micron particle size range. These finely divided particles apparently adhere to the desired 1-200 micron particles, making their removal difficult. While not wishing to be bound by any theory, these finely divided particles are believed to adhere to the desired 1-200 micron particles by electrostatic type interactions, e.g., van der waals forces.

In any event, the presence of these finely divided particles adversely affects the ultimate performance of the 1-200 micron particles in a slurry Fischer-Tropsch process for the production of heavy hydrocarbons. These particles can be entrained in droplets of liquid that are carried over with the gaseous stream that exits the reactor, thereby leading to contamination of downstream equipment, and they can interfere with the efficient separation of the 1-200 micron particles from the heavy (non-volatile) hydrocarbon products. This is especially true if the catalyst-product separation procedure involves filtration.

In the process of the instant invention, the predominantly 1-200 micron catalyst particles are first dispersed in a liquid comprising either (a) a hydrocarbon such as a paraffin comprising a saturated linear, branched or cyclic hydrocarbon containing from 5 to over 100 carbon atoms or mixtures thereof, or a molten paraffin-rich Fischer-Tropsch wax, with a small amount of a material acting as a surfactant, e.g., water, or a surfactant as described below thereof, or (b) protic liquids which may comprise water, aliphatic alcohols such as methanol, ethanol or higher alcohols, ketones, aldehydes, esters, carboxylic acids and the like which contain added surfactant molecules. Protic liquids are those that contain at least one hydroxyl (-OH) group.

The liquid is preferably, essentially free of contaminants such as trace metals, halides, phosphorus, sulfur or nitrogen, which may be present at levels less than 1000 ppm by weight. If polar protic components are not present in the liquid they can be added. Aqueous or hydrocarbon liquids can be employed to which polar protic molecules are added. A range of polar protic molecules can be employed such as mono and poly-carboxylic acids, alcohols, hydroxycarboxylic acids, hydroxyketones, glycols, hemiacetals, and the like. Mono- and poly-carboxylic acids such as acetic acid, propionic acid, butyric acid, palmitic acid, stearic acid, benzoic acid, adipic acid, lactic acid, tartaric acid, glycolic acid, oleic acid, and related compounds can be used without departing from the scope of this invention. Alcohols such as methanol, ethanol, propanol, butanol, ethylene glycol, erythritol, and various polyalkylene glycol derivatives can also be used within the scope of this invention. Other oxygenated molecules such as hydroxyesters can be used with the proviso that they contain hydroxy moieties, i.e., -OH groups, within their molecular structure. These components can be added alone or in combination without departing from the scope of the present invention.

Paraffin solvents useful in the instant process can be derived from petroleum or synthesized from coal, shale, tar sands, natural gas or other carbonaceous feed stocks. The liquid can be stored in air, and may contain low levels of oxygen-containing products in the range of 0.01 to about 2% wt.

Surfactant molecules can be added to the liquids used in this invention, especially the polar protic solvents, in order to improve the overall efficiency of catalyst pretreatment step. Surfactants such as alkali salts of fatty acids, alkylsulfonic acids alkylbenzenesulfonic acids, alkylnapthalenesulfonic acids, and the like are useful. Long chain amines, diamines and polyamines can also be used as well as polyoxyalkylated analogs. Oxyalkylated alkylphenols, polyalkylphenols, alkanolamines, sorbitols and polyalkalkylene oxide derivatives of these molecules can also be employed. Long chain polyols and alkyl ether substituted derivatives can be employed alone or together with mixtures of the surfactants listed above. Other examples of surfactants useful in the practice of the instant invention are listed in "Detergents and Emulsifiers" from McCutcheon Publishing, Glen Rock, N.J. (1977). Surfactants such are as fatty acids, e.g., oleic acid and commercially available compounds such as the dioctyl ester of sodium sulfosuccinic acid (Aerosol OT-100) are preferred in the present invention.

The amount of surfactant or surfactant-like material employed is that which is sufficient to help effect the separation which is believed to occur by overcoming the electrostatic forces binding the sub micron particles to the catalyst particles. Usually 15% or less of surfactant or surfactant like material is employed.

The initial mixture contains catalyst powder, e.g., 6% wt. Co and 1% wt. Re on titania, with a powder loading level of from 0.5 to 50% wt, preferably from about 2 to 10% wt. The mixture is agitated either mechanically or ultrasonically or by other methods to insure good stirring and contact between the solid and liquid phases. The method can be effected at room temperature or temperatures up to about 200° C. may be employed; that is, temperatures below which there is decomposition of any of the materials employed in the method. Preferred are about 50° to 200° C., more preferably from about 100° to 150° C., and most preferably from about 115° to 135° C. Agitation or stirring of the mixture is continued for a period of time under ambient conditions, e.g., an oxygen, nitrogen or air containing environment, for a period sufficient to concentrate the submicron particles in the liquid phase. The preferred contact time is from about 1 hour to several days, preferably from about 15 to 72 hours, but sufficient to separate sub micron particles from the catalyst particles. Stirring of the mixture can be periodically stopped, allowing the desired 1-200 micron particle to settle to the bottom of the vessel and the supernatent liquid, containing the finely divided sub 1 micron particles, to be decanted or otherwise separated. Additional liquid components can be added and the cycle of, stirring or agitating the mixture, allowing it to settle and separating the fines containing phase, can be repeated several times to insure removal of the sub 1 micron particles. The number of these liquid addition, agitating, settling, decanting cycles will be determined in part by the state of the initial catalyst powder. The efficiency of each cycle can be determined by the weight of catalyst isolated after the decanting step, and the optimum number of cycles will be defined as that number which gives a constant weight of catalyst recovered relative to the previous cycle, i.e., when sub 1 micron particles are no longer being removed by additional cycles. Usually 2 to 3 cycles are required to remove over 80% wt of the finely divided sub 1 micron particles, and this appears to be adequate for most applications.

The amount of liquid used should be at least enough to cover the particles to be treated, preferably with at least a 100% excess or more.

EXAMPLES

Preparation of Co-Re/TiO$_2$

A cobalt-rhenium on titania catalyst is used to illustrate the advantages of the pretreatment procedure of the instant invention. This catalyst is prepared by a method previously disclosed in U.S. Pat. No. 4,568,663 issued on Feb. 4, 1986. Samples of catalyst pellets are crushed and then sieved to collect particles with average diameter between 40 and 200 microns. This material is used in the examples described below.

Fischer-Tropsch Wax

The Fischer-Tropsch wax used in Examples 1-4 was prepared from carbon monoxide hydrogenation over a Co-Re catalyst on a titania containing support. The carbon distribution of the sample used is shown in Table 1 below.

TABLE 1

| Carbon Number Distribution Of Fischer-Tropsch Wax | |
|---|---|
| Carbon Number Range | Concentration (wt. %) |
| 6-10 | 8.1 |
| 10-20 | 28.0 |
| 21+ | 63.9 |

Note:
The sample was found to contain less than 0.05% wt concentration of alcohols/oxygenated components.

Catalyst Filtration Studies

Example 1—Filtration of Untreated Catalyst Powder

A sample of 3.5 grams of powdered catalyst was added to 35 grams of Fischer-Tropsch wax and the mixture heated to 140° C. in a heating oven. After the wax had melted the mixture was stirred and then allowed to stand for 2 hours in contact with the molten wax. The sample was then placed in a Millipore vacuum filtration apparatus (0.45 micron pore filter paper) and filtered to form a filter cake. After the cake had formed, a fresh 50 gram sample of molten Fischer-Tropsch wax was filtered through it and the filtration time required for passage of 50 grams of wax was measured. The results of this experiment are shown in Table 2.

The results of this example clearly show the limited filter performance for wax-solids separation, when the solids have not been pretreated according to the process of the instant invention. These results are similar to those previously reported by Farley et al in The Journal of the Petroleum Institute, Vol. 50, February (1964) for a series of iron based powdered catalysts.

Example 2—Filtration of Water Pretreated Catalyst Powder

A sample of 15 grams of powdered catalyst was placed in a glass container with 85 grams of water. The mixture was agitated at room temperature for about 2 minutes and then allowed to settle. After the particles settled, the upper aqueous phase was found to be opaque and was separated by decanting. Additional water was added to the mixture, it was stirred, allowed to settle and then decanted for an additional five times. The catalyst containing phase was then mixed with equal volumes of acetone, allowed to settle and decanted an additional two times, and the remaining solids filtered on the 0.45 micron filter. The filter cake was allowed to dry and the time for passage of 50 grams of molten Fischer-Tropsch wax determined, see Table 2.

Example 3—Filtration of Oleic Acid Pretreated Catalyst Powder

A sample of 10 grams of powdered catalyst was added to 150 ml of 1% wt. oleic acid in a 1/9 vol/vol mixture of isopropanol and heptane. The mixture was agitated for 1-2 minutes and then allowed to stand. The upper, milky liquid phase was separated by decanting and additional amounts of the oleic acid in isopropanol and heptane were added, the system was agitated, allowed to settle and the upper phase decanted for a total of seven such cycles. The catalyst containing phase was then treated with an equal volume of acetone with the system then agitated, allowed to settle and decanted for an additional two cycles. The catalyst containing phase was filtered through the 0.45 micron filter, the cake dried and then subjected to the same filtration test as performed in Example 2. The results are shown in Table 2.

Example 4—Filtration of Aerosol-OT-100 Pretreated Catalyst Powder

A 10 gram sample of catalyst powder was placed in 150 ml of a solution of 1% wt. Aerosol-OT-100 in a 1/9 vol/vol mixture of isopropanol and heptane. The mixture was agitated for 1-2 minutes and then allowed to stand. The upper, milky liquid phase was separated by decanting and additional amounts of the Aerosol-OT-100 in isopropanol and heptane were added, the system agitated, the slurry allowed to settle and the upper phase decanted for a total of seven such cycles. The catalyst containing phase was then treated with and equal volume of acetone, the slurry agitated, allowed to settle and the upper phase decanted for two such cycles. The catalyst containing phase was then filtered through the 0.45 micron filter, the cake dried and then subjected to the same filtration test as performed in example 2. The results are shown in Table 2.

TABLE 2

| Catalyst Filtration Results | | |
|---|---|---|
| Example | Filter Time[1] (minutes) | Filter Rate (gm/min) |
| 1 | 95.0 | 0.5 |
| 2 | 0.9 | 55.0 |
| 3 | 1.0 | 50.0 |
| 4 | 1.0 | 50.0 |

[1]Time required for passage of 50 grams of molten Fischer-Tropsch wax (140° C.) through the filter cake.

The results of Examples 2, 3, and 4 clearly demonstrate the beneficial effects of the pretreatment procedure of the instant invention in preparing a catalyst for operation in a slurry Fischer-Tropsch process for the continuous production and removal of paraffin wax. The filtration rates achieved through catalyst which has been pretreated with a polar protic component to remove finely divided sub 1 micron particles is nearly two orders of magnitude greater than than achieved with catalyst powders that have not been pretreated according to the process of this invention.

On completion of this pretreatment step, the desired 1-200 micron catalyst particles can be isolated by filtration, centrifugation or other traditional separations techniques. This material can be washed with an inert light hydrocarbon such as pentane, hexane or the like and dried in a vacuum chamber or by exposure to flowing gas such as air, nitrogen, oxygen, helium and the like. The catalyst powder is then ready for storage or for direct use in the next pretreatment step involving activation with an oxidizing or reducing gas, and subsequent transfer to the slurry reactor system.

Fischer-Tropsch Wax

The wax used in Examples 5-7 was prepared by hydrogenation of carbon monoxide over a cobalt-rhenium catalyst supported on a titania containing support. The melting point of the wax used was in the range of 110° C. to 120° C. The composition of the wax used is described in Table 3.

TABLE 3

| Carbon Number Range | Conc. Wt. % | Percent As | | | |
|---|---|---|---|---|---|
| | | n-Paraffin | Olefin | Alcohol | Other |
| 1-10 | 0.44 | 59.8 | 11.6 | 1.8 | 26.8 |
| 11-20 | 13.49 | 88.1 | 5.9 | 1.4 | 4.7 |
| 21-30 | 19.52 | 98.4 | 0.0 | 0.6 | 1.0 |
| 31-40 | 15.58 | 91.8 | 0.0 | 0.0 | 8.2 |
| 41-50 | 10.49 | — | — | — | — |
| 51-75 | 20.26 | — | — | — | — |
| 76-100 | 8.55 | — | — | — | — |
| 101-125 | 4.27 | — | — | — | — |
| 126-150 | 2.66 | — | — | — | — |
| 151-200 | 2.68 | — | — | — | — |
| 201-300 | 1.72 | — | — | — | — |
| 301-400 | 0.28 | — | — | — | — |
| 401+ | 0.11 | — | — | — | — |

Note:
Components identified as "other" consist primarily of branched paraffins.

Catalyst Filtration Studies

Example 5

A Co-Re/$TiO_2$ catalyst containing 6% wt. cobalt and 1% wt. rhenium was sieved to remove particles of nominally less than 44 micron and greater than 180 micron average diameter. Two volume percent of this catalyst was suspended in molten Fischer-Tropsch wax at 130° C. containing hydrocarbon molecules which contain from about 6 to about 400 carbon atoms per chain. After stirring this mixture in air for about 5 minutes, the initial filtration rate was measured through a 0.3 micron glass fiber filter, Gelman Type A/E 47 mm diameter, at a filter differential pressure of 14 psig. A filtration rate equivalent to 5.8 gal of liquid per square foot of filter surface area per minute (gal/$ft^2$/min) was obtained. Stirring was continued for an additional 44 hours in air or nitrogen, or mixtures of air and nitrogen, for a series of samples and the filtration rates again measured. Maximum filtration rates of about 0.05 gallons of liquid per square foot of filter surface per minute (gal/$ft^2$/min) were obtained.

Example 6

Two volume percent of the Co-Re/$TiO_2$ catalyst described above was added to the stirred molten Fischer-Tropsch wax described in Table 1. After stirring for 10 minutes at 170° C. a filter rate of 1 gallon per square foot of filter surface area per minute (gal/$ft^2$/min) was obtained at a differential pressure of 14 psig using a cylindrical, 1 inch diameter by 3 inch long, Rigimesh filter element with 18 micron pores. After stirring for 2 hours at 170° C. under nitrogen, the slurried catalyst powder filtered at a rate of less than 0.01 gallons per square foot of surface area per minute over the Rigimesh filter with a differential pressure of 14 psig. The original filtration rate could not be restored by backflushing the filter with molten Fischer-Tropsch wax. In this backflushing procedure, 1 liter of filtered wax is forced backwards through the filter into the slurry mixture at a pressure of 30 psig in an attempt to remove finely divided catalyst particles which have clogged the pores of the filter element. Five minutes after the backflushing procedure was completed, a filtration rate of less than 0.01 gallons per square foot of filter surface area per minute was obtained at 170° C. with a differential pressure of 14 psig.

These results clearly show the degradation of filter performance with time in the process of wax-solids separation, when the solids have not been pretreated according to the process of the instant invention. These results are similar to those previously reported by Farley et al in The Journal of the Petroleum Institute, Vol. 50, February (1964) for a series of iron based powdered catalysts.

Pretreatment Procedure for Sub 1 Micron Particle Removal

Example 7

Two volume percent of an identical sample of catalyst as in Examples 5-7 was stirred for 19 hours under nitrogen at 120° C. in Fischer-Tropsch wax. The suspension was allowed to settle for about 5 minutes and the opaque liquid layer was decanted from the settled solids. Approximately 90% vol. of the molten wax was removed. Fresh wax was added to the settled solids to restore the initial volume of the suspension. The solid-wax suspension was stirred for an additional 48 hours at 120° C. under nitrogen, allowed to settle for about 5 minutes, and then decanted as before. Fresh wax was again added to the solids to restore the initial volume of the suspension. After stirring for 24 hours at 120° C. under nitrogen with stirring, this suspension filtered at a rate equivalent to 14.5 gallons of liquid per square foot of filter surface per minute (gal/$ft^2$/min) through the 1 micron glass filter element. Approximately 85% wt. of the originally charged solids were recovered on the filter pad. The remaining 15% wt. of material not recovered, which consisted primarily of finely divided sub 1 micron particles, having been removed in the course of this process.

The number of cycles of stirring, decantation, addition of fresh wax can be chosen so as to remove the majority of these finely divided sub 1 micron particles. The number of cycles can be established by determining the the point at which additional cycles give an essentially equal recovery efficiency to that obtained in the previous cycle. The number of cycles will in part be determined by the level of finely divided sub 1 micron particles that were present in the original sample, the actual particle size distribution of these sub 1 micron particles in the original sample, the physical and chemical properties of the Fischer-Tropsch wax, and the settling time before decantation in each cycle.

These results clearly demonstrate the beneficial effects of the pretreatment procedure of the instant invention in preparing a catalyst for operation in a slurry Fischer-Tropsch process for the continuous production and removal of paraffin wax.

On completion of this pretreatment step, the desired 1–200 micron catalyst particles can be isolated by filtration, centrifugation or other traditional separations techniques. This material can be washed with an inert light hydrocarbon such as pentane, hexane or the like and dried in a vacuum chamber or by exposure to flowing gas such as air, nitrogen, oxygen, helium and the like. The catalyst powder is then ready for storage or for direct use in subsequent pretreatment steps involving activation with an oxidizing or reducing gas, and subsequent transfer to the slurry reactor system.

What is claimed is:

1. A liquid phase method for removing sub-1 micron particles adhering to catalyst particles the catalyst containing a Group VIII metal supported on an inorganic refractory oxide as a result of preparation of the catalyst which comprises:
   (a) dispersing the catalyst particles to which the sub-1 micron particles adhere within a liquid comprising a Fischer-Tropsch;
   (b) agitating the dispersion and separating the sub-1 micron particles from the catalyst particles, and concentrating the sub-1 micron particles in the liquid phase; and
   (c) separating the sub-1 micron containing liquid phase from the particulate material.

2. The method of claim 1 wherein the Fischer-Tropsch wax is substantially free of oxygenated compounds.

3. The method of claim 2 wherein the presence of oxygenated products is less than about 2 wt %.

4. The method of claim 1 wherein the catalyst particles range in size from 1–200 microns.

5. The method of claim 1 wherein a surfactant is present in the liquid.

6. The method of claim 5 wherein the surfactant is a fatty acid.

7. The method of claim 1 wherein the inorganic oxide is selected from the group consisting of titania, silica, alumina, silica-alumina, and titania-alumina.

8. The method of claim 7 wherein the particulate material is a catalyst comprising cobalt on titania.

9. The method of claim 1 wherein subsequent to step (c) one or more cycles of additional liquid is contacted with the catalyst and steps (b) and (c) are repeated.

10. The method of claim 9 wherein the recovered catalyst is free of at least 80% of the sub micron particles.

* * * * *